United States Patent [19]
Fischer et al.

[11] Patent Number: 6,073,491
[45] Date of Patent: Jun. 13, 2000

[54] METHOD AND ARRANGEMENT FOR MAKING CONTACTLESS DISTANCE AND PRESSURE MEASUREMENTS WITHIN AN AIR SPRING

[75] Inventors: Norbert Fischer, Sehnde; Roland Altsinger, Burgdorf, both of Germany

[73] Assignee: ContiTech Luftfedersysteme GmbH, Hannover, Germany

[21] Appl. No.: 09/307,873

[22] Filed: May 10, 1999

[30] Foreign Application Priority Data

May 9, 1998 [DE] Germany .............. 198 20 877

[51] Int. Cl.⁷ .................................. G01N 29/00
[52] U.S. Cl. .................. 73/629; 73/618; 73/632; 267/64.19
[58] Field of Search .................. 73/290 V, 597, 73/627, 629, 862.581, 862.59, 862.621, 862.625; 267/256, 64.11, 64.19, 64.28; 280/5.5, 5.514, 5.515, 6.15, 6.157, 6.159, 124.157, 124.158, 124.159; 340/614, 626; 356/4.01, 4.08; 367/902, 908

[56] References Cited

U.S. PATENT DOCUMENTS

| | | | |
|---|---|---|---|
| 2,743,429 | 4/1956 | Erdman et al. | 340/1 |
| 3,543,649 | 12/1970 | Head et al. | 367/96 |
| 4,561,064 | 12/1985 | Brüggen et al. | 364/561 |
| 4,798,369 | 1/1989 | Geno et al. | 267/64.11 |
| 4,938,066 | 7/1990 | Dorr | 73/597 |
| 5,707,045 | 1/1998 | Easter | 267/64.21 |
| 5,859,692 | 1/1999 | Ross, Jr. et al. | 356/4.01 |
| 5,936,161 | 8/1999 | Fischer | 73/632 |

FOREIGN PATENT DOCUMENTS

| | | |
|---|---|---|
| 3423602 | 1/1986 | Germany . |
| 3620957 | 1/1987 | Germany . |
| 8702817 | 6/1987 | Germany . |

*Primary Examiner*—Hezron Williams
*Assistant Examiner*—Rose M. Miller
*Attorney, Agent, or Firm*—Walter Ottesen

[57] ABSTRACT

The exact spring height as well as the spring pressure can be determined with a single arrangement for the optimal utilization of the axle loads of a multi-axle air spring suspended vehicle and to control the distance between the chassis and the axle. An air spring (2) is equipped with an ultrasonic pulse/echo measuring system. The air spring (2) includes a transmitter/receiver component (14) arranged on the chassis and a first reference electrode (20) and a reflector component (16) fixed to the axle. The air spring height can be determined in a conventional manner from the relative value of the running times of the ultrasonic pulses which are traversed on the reference path and the measuring path. A second reference reflector (22) is mounted at a different distance to the first reference reflector (20). For the determination of pressure, the transmitting power or the receiving amplification of the second reference reflector (22) is controlled in such a manner that the amplitude (intensity) of the sonic waves, which are reflected from the first reference reflector (20), remains at a constant value. This amplitude (intensity) is measured via the sonic transducer (14).

5 Claims, 3 Drawing Sheets

METHOD AND ARRANGEMENT FOR MAKING CONTACTLESS DISTANCE AND PRESSURE MEASUREMENTS WITHIN AN AIR SPRING

FIELD OF THE INVENTION

The invention relates to an ultrasonic pulse/echo method and an apparatus for making contactless measurements of the distance between the axle and the chassis of an air-spring suspended vehicle.

BACKGROUND OF THE INVENTION

Air springs are mounted between the axle and the chassis as supporting parts in a vehicle. The distance between the chassis and the axle should not change even for different loading conditions. For this reason, it is necessary to measure the air spring height and to readjust the system by pumping and venting air when there are deviations. An air spring control is also necessary for multi-axle vehicles for optimally utilizing the axle loads.

The invention relates to an air spring wherein the particular traveling elevation is determined with the aid of an ultrasonic running-time measurement within the air spring while utilizing at least one reference distance.

An ultrasonic distance measurement is utilized, for example, for the fill level measurements of vessels, to measure rooms in a building, to measure distance when parking a motor vehicle and to measure distance in autofocusing photo apparatus et cetera.

German patent publication 3,423,602 discloses an arrangement for measuring the distance between the chassis and the axle of a vehicle while utilizing an ultrasonic measurement system configured as a transmitter/receiver. The advantages of using ultrasonic sound within an air spring is that there is no turbulence of the sound wave within the air spring chamber because of the driving wind and the overpressure, which is present in the air spring, makes a very good range of the ultrasonic waves possible even at higher frequencies.

On the other hand, for distance measurement within the air spring chamber, the problem is present that pressure differences between 0 and approximately 20 bar and temperature ranges between −40° C. and +120° C. must be mastered. The speed of sound in a real gas (here, pumped-in air) is dependent to a great extent on temperature and to a lesser extent on pressure. For this reason, significant errors occur when making the distance computation based on a fixed pregiven sonic velocity.

To avoid errors, U.S. Pat. No. 4,798,369 suggests a compensation of pressure and temperature dependency by means of a computer circuit. However, how this is to be done is not disclosed in detail.

German patent publication 3,620,957 discloses an air spring having an ultrasonic pulse/echo system for making elevation measurements. An additional fixed target is suggested in order to cancel the effects of running speed changes of the pulse which can occur because of changes in air pressure, temperature and humidity within the air spring. In this way, a relative value of the running times is determined. A knowledge of the instantaneous sonic velocity is not required for computing the driving elevation.

The disadvantage in such a relative method while utilizing a reference distance (as known in a comparable manner from a telescope shock absorber disclosed in German patent publication G 87 02 817.4) is especially that the significant quantities of pressure and temperature cannot be explicitly indicated. German patent publication G 87 02 817.4 only suggests that thermistors be installed for temperature compensation. Here too, details are not presented.

The spring pressure, which is of interest for the loading state of the vehicle (the wheel load et cetera), cannot be determined with any of the above-mentioned air spring measurement arrangements.

Air spring systems are in use wherein separate pressure sensors operating on a DMS (resistance strain gauge) basis or piezo transducers are provided to measure pressure within the air spring volume. With these sensors, mechanical deformations of a membrane cause a change of resistance of the applied resistance elements or a displacement of electrical charges.

U.S. patent application Ser. No. 09/006,442, filed Jan. 13, 1998, discloses an arrangement for making contactless distance and pressure measurements within an air spring. Here, an ultrasonic arrangement comprises a transmitter/receiver component mounted on the chassis and a first reflector for forming a first reference distance $s_{r1}$ and a reflector fixedly mounted on the axle 4 defining a measuring distance $s_{r2}$. The transmitter/receiver component with the first reflector is elastically mounted in a pipe stub fixed to the chassis. A second reflector is fixedly mounted on the pipe stub and defines a second reference distance $s_{r2}$.

By comparing the running times, which are assigned to the two reference distances as $s_{r1}$ and $s_{r2}$, the displacement of the elastically mounted sonic transducer is obtained and the internal pressure in the air spring can be determined.

The yielding of the elastic suspension constitutes a decisive factor for determining the pressure. For this reason, a high precision is required with reference to maintaining the geometric dimensions of the acoustic position as well as its embedment. The surface of the elastic mounting should always be kept clean to avoid a negative effect on the elasticity of the embedment by dirt. No investigative results are presented with reference to the resistance to deterioration of the elasticity module.

SUMMARY OF THE INVENTION

It is an object of the invention to provide an air spring having an ultrasonic-pulse/echo measuring system with which the exact height of the air spring as well as the pressure present therein can be determined with a single arrangement or method. In this context, the use of elastic material should be substantially avoided.

The pulse/echo method of the invention is for making contactless measurements of the spacing between the axle and the chassis of an air spring suspended vehicle and to measure the pressure present in the air spring. The method includes the steps of: providing an ultrasonic arrangement including a transmitter/receiver component mounted on the chassis, a first reference reflector disposed at a first distance to the transmitter/receiver component and an end reflector fixedly mounted at the axle; providing a second reference reflector disposed at a second distance to the transmitter/receiver component with the second distance being different from the first distance; determining the spacing from a relative value of the running times of the ultrasonic pulses traversing the first and second distances; converting sound reflected from the first and second reference reflectors into first and second sonic signals; providing a control unit for controlling one of the transmitting signal power and the receiving amplification of the sonic signals to determine the pressure in the air spring; adapting the control unit to control the one of the transmitting signal power and the amplification of the sonic signals so that the amplitude of the sound waves reflected from the first reference reflector remains at a constant value; measuring the echo amplitude of the second reference reflector utilizing a first unit; and, determining the pressure in the air spring from the echo amplitude measured from the second reference reflector with the aid of an amplitude/pressure characteristic line and the instantaneous temperature.

According to the invention, the air pressure, which is required to determine the actual sonic velocity present in the air chamber, is not determined by a separately mounted pressure sensor; instead, the invention proceeds from the realization that the air pressure, which is present in the air spring, has a direct effect on the amplitude of the received ultrasonic signal.

Thus, the pressure, which is present in the air spring, is not determined by a separate pressure sensor; instead, the pressure is determined from the fact, which is known from acoustics, that the air pressure has an effect on the absorption performance of real gases and therefore on the amplitude of the received ultrasonic signal. To measure the pressure, the invention therefore suggests especially the use of two ultrasonic reference distances. With the supplement of a second reference distance, the simultaneous determination of the height h and of the pressure p is possible simultaneously. The height h or spring height is, for example, the distance between the sonic transducer mounted in the pipe stub and the reflector mounted on the axle or axle bumper.

The invention utilizes the known fact that a running-time measuring arrangement can be used to determine the distance between the axle and the chassis. This running-time measuring arrangement includes an ultrasonic transmitter and an ultrasonic sensor mounted within the air spring chamber. The invention utilizes a measuring system for determining the spring height from the running time of an ultrasonic signal while considering the pressure present in the air spring.

According to an embodiment of an arrangement of the invention, the running time of the ultrasonic signal as well as the pressure present in the air spring are determined with a single apparatus. Here, the sonic running time is measured in a manner known per se in accordance with the pulse/echo method. For the determination of the air spring internal pressure, the effect is utilized in accordance with which the sound intensity of the echo signal is dependent upon the particular pressure present in the air spring. An increase in pressure effects an increase of the level of the echo signal. Thus, the pressure present in the air spring is not determined with the aid of a separate pressure sensor; rather, the pressure is determined from the fact known from acoustics that the air pressure has an effect on the absorption performance of real gases and therefore on the amplitude of the received ultrasonic signal.

The sound amplitude detected by the ultrasonic sensor is not only dependent upon the pressure within the air spring but also on the configuration of the sonic transducer, the acoustic adaptation, the supply voltage and other influencing quantities. For this reason, with the aid of a control unit and a first reference reflector, it is ensured that the measured intensity of the echo, which is reflected from this reflector, always remains constant.

For the above, either the transmitting power or the amplification is controlled. Now, the echo amplitude reflected by the second reference reflector is measured. Together with a temperature value, which is estimated from the running time, the pressure is computed which, in turn, serves for a precise determination of the actual given sonic velocity and finally for the determination of the spring height. More specifically, in addition to the determination of the spring height, the determination of the parameter "pressure" is also possible at the same time with a single apparatus.

Preferably, the first and second reflectors are formed by first and second segments of exposed wire. The wire reflectors according to the invention have a greater stability than a metal disc attached to a stem. This is especially significant in rough driving operation as is the case with a motor vehicle. The reflectors made of wire are especially simple and inexpensive to produce.

BRIEF DESCRIPTION OF THE DRAWINGS

The invention will now be described with reference to the drawings wherein:

FIG. 3$b$ shows the strong dependency of the sonic velocity c on the temperature T;

FIG. 3$c$ shows the dependency of the sound conduction (intensity I) on pressure p; and, FIG. 3$d$ shows the influence of the temperature T on the sound conduction (intensity I).

DESCRIPTION OF THE PREFERRED EMBODIMENTS OF THE INVENTION

Figure 1:
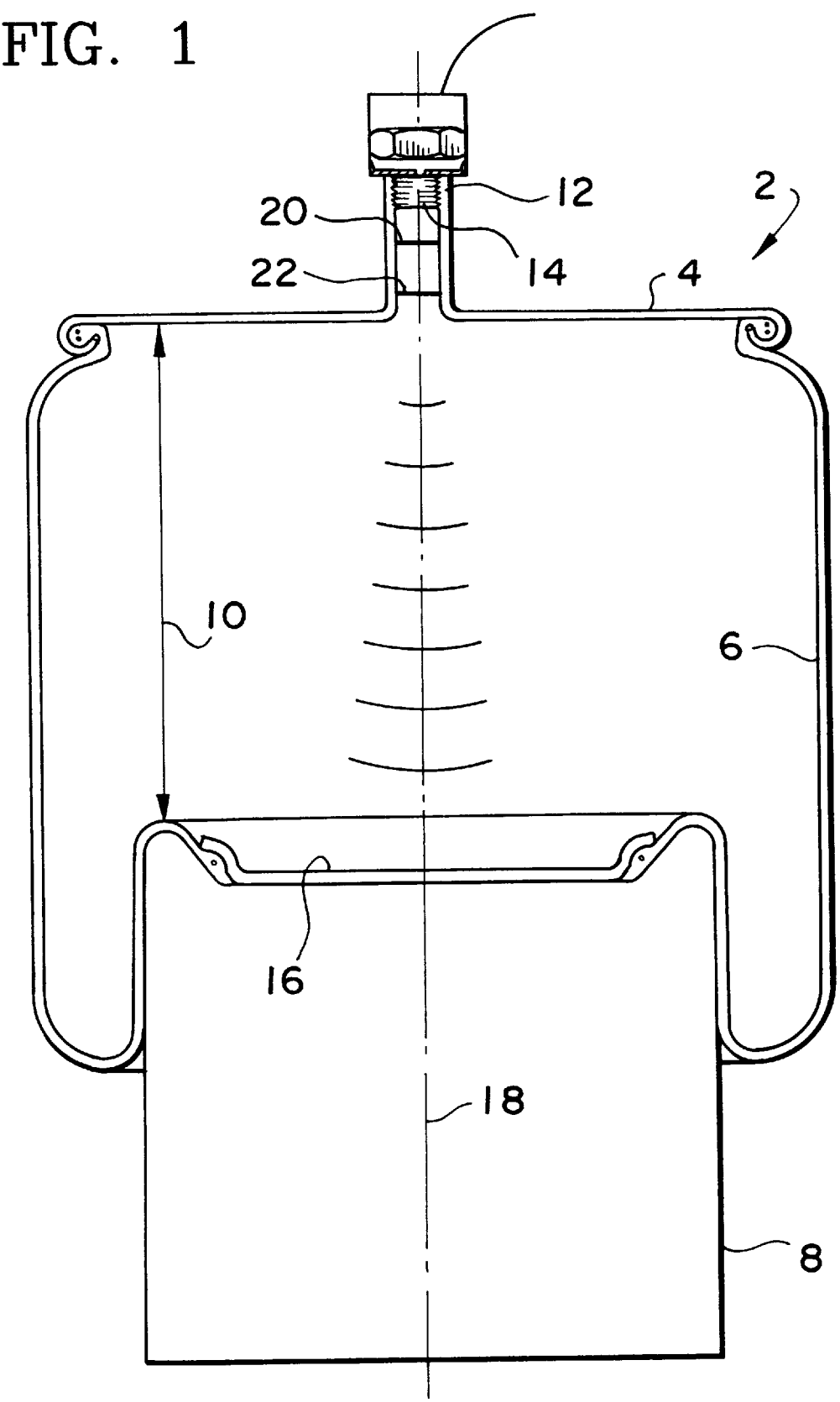
FIG. 1 is a longitudinal section view of an air spring provided with a measuring system according to the invention.

An air spring 2 conventionally includes essentially a cover plate 4, a roll-off piston 8 and a flexible member 6 which defines a rolling lobe as the flexible member rolls up and down on the piston 8. The cover plate 4 is fixedly attached to the longitudinal beam of the vehicle chassis (not shown). The roll-off piston 8 is attached to the axle. The flexible member 6 rolls on the roll-off piston as the air spring suspends the vehicle and the clear distance 10 between the cover plate 4 and the roll-off piston 8 changes. It is this distance which is to be measured. For this purpose, and according to the invention, a pipe stub 12 is provided in the cover plate 4 with an ultrasonic component 14 mounted in the pipe stub. The ultrasonic component 14 is configured as a transmitter and receiver.

A temperature sensor (not shown) can be mounted next to the ultrasonic transducer 14 for measuring the temperature in the air spring. The temperature sensor can be mounted, for example, as disclosed in U.S. Pat. No. 5,936,161 now U.S. Pat. No. 5,936,161, and incorporated herein by reference.

The pipe stub 12 is so configured that the clear space between the ultrasonic component 14 and the surface 16 is unobstructed. In the rebounded state of the air spring 2, the pipe stub 12 is directed toward the center of the clamping plate. At the clamping plate, a reflector component 16 is provided which can be part of a conventional rubber bumper.

A first reference reflector 20 and a second reference reflector 22 are disposed in the pipe stub 12 with each reflector being transverse to the axis 18 of the air spring. These reflectors (20, 22) can be configured as simple segments of exposed wire.

Figure 2:
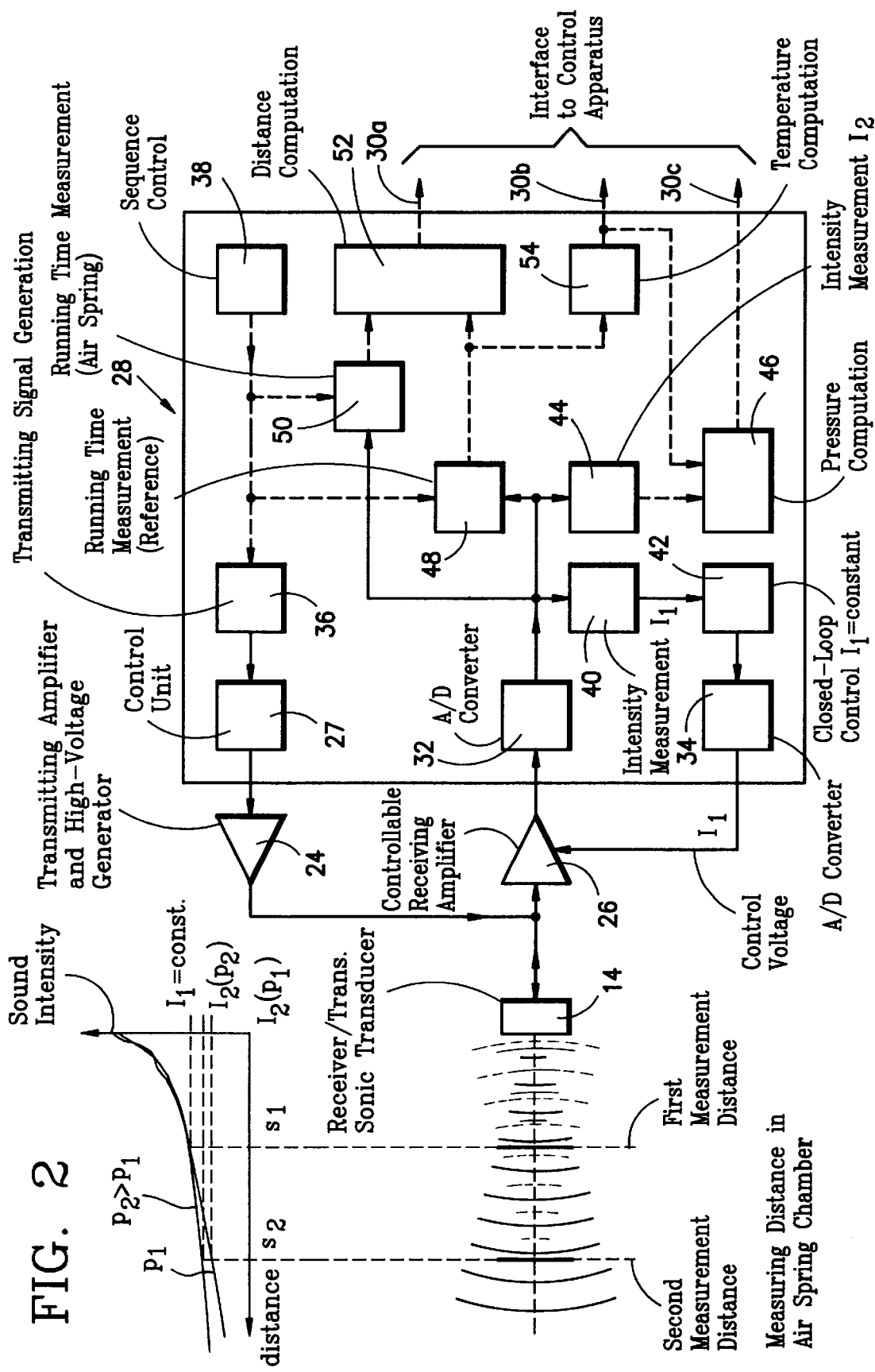
FIG. 2 is a block circuit diagram of the electronics provided for the measuring system of the invention.

The electronic circuit provided for the measurements is shown in FIG. 2 and includes the following components: a sonic transducer 14, a transmitter amplifier 24 including high voltage generation, a controllable receiver amplifier 26 and a microprocessor 28 having interfaces 30a, 30b and 30c to a control apparatus (not shown).

The microprocessor 28 includes the following function elements: two analog-to-digital converters (32, 34), transmitter signal generation 36, sequence control 38, intensity measurement $I_1$ (40), control $I_1$=constant (42), intensity measurement $I_2$ (44), pressure computation 46, running-time measurement (reference) 48, running-time measurement (air spring) 50, distance computation 52 and temperature computation 54.

The operation of the system shown in FIG. 2 will now be explained.

According to the invention, and with the aid of a control unit 27, it is ensured that the measured intensity of the echo, which is reflected back from the first reflector 20, always remains constant. The control unit 27 controls the voltage of the transmitting signal generated in block 36. For this purpose, either the transmission power or the amplification is correspondingly controlled. This control unit for holding the intensity of the reflected echo constant can comprise a controller of the transmitter amplifier 24. However, the control unit could also be assigned to the transmitting signal generation 36. It is also possible to provide for the adaptation of the received echo signal in the controllable receiving amplifier 26. In the case of control unit 27, the pressure p is computed from the determination of the change of intensity while considering the I/p function shown in FIG. 3c.

This intensity control of the echo is necessary for the following reasons:
 a) to eliminate influences of the pressure on the sonic power radiated from the transducer (for example, if the embedding mass or its damping performance is dependent upon temperature); and,
 b) to eliminate the effects of deterioration (deterioration of the embedment mass and sealing mass).

At the same time, the first reference distance is applied to calibrate the distance measurement and is used for the temperature measurement.

Furthermore, the echo amplitude, which is reflected from the second reference reflector 22, is measured. Together with the temperature value derived from the running-time computation, the pressure in the air spring chamber can be computed from the echo amplitude. This pressure, in turn, serves for the precise determination of the actual sonic velocity and finally for the determination of the spring height.

The temperature value can be derived directly from the running time of the reference echo. The pressure does not have to be applied for determining the spring height.

Accordingly, the precise distance and the precise temperature can be determined from the running time within the air spring and the running time of one of the two reference distances and the pressure can be computed from the attenuation between the first and second reference distances and the temperature. That is, without knowledge of the sonic velocity, the spring height can be determined in a conventional manner from the ratio of the running times of the measuring distance $s_x$ to the reference distance $s_{r1}$. In this connection, reference can be made to German patent publication 3,620,957.

Also, the echo running time of one of the two reference reflectors (20, 22) can be used in order to calibrate the distance measuring system and in order to measure the temperature in the air spring chamber enclosed by flexible member 6.

Knowledge as to the pressure present instantaneously in the air spring 2 serves, for example, as the basis of the computation of the loading state or of the particular wheel load.

Figure 3A:
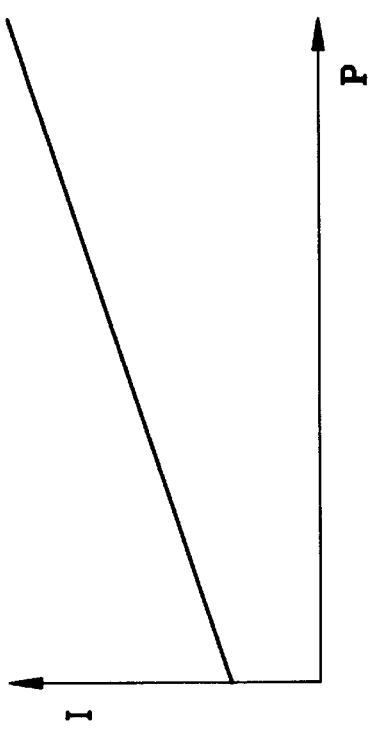
FIG. 3$a$ is a graph showing the very slight dependency of the sonic velocity c on pressure p.
Figure 3C:
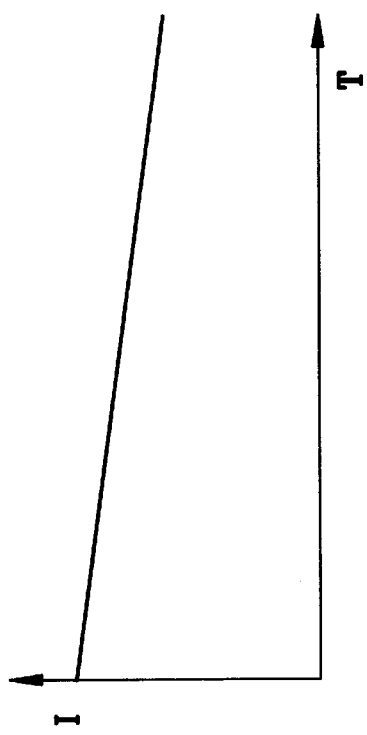
Figure 3B:
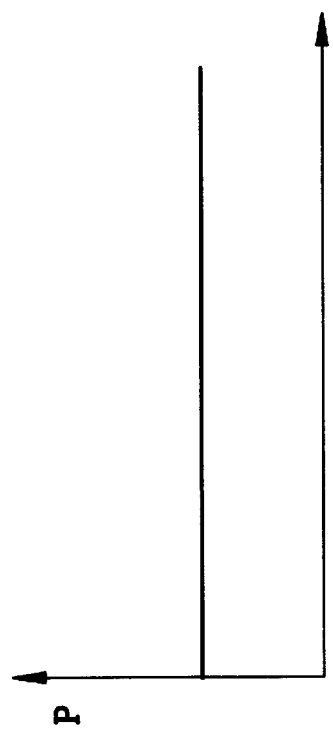
Figure 3D:
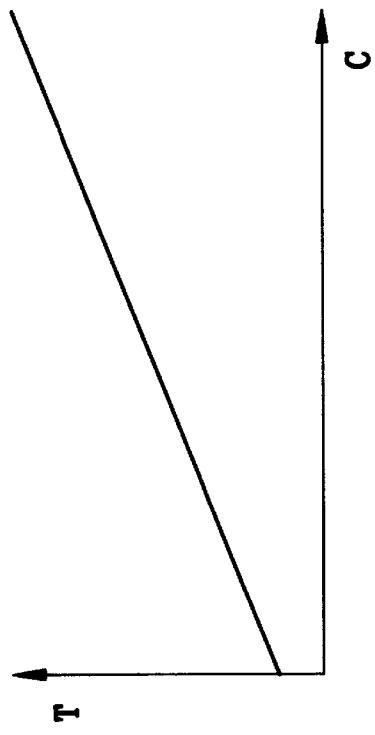

As shown in FIG. 3b, the sonic velocity c (that is, the running time t of an ultrasonic pulse running back and forth between the transmitter/receiver component 14 and a reference reflector 20 or 22) is dependent on temperature T. More specifically, the sonic velocity can be determined from the measured running time and double the path distance between transducer and reflector in order to compute the temperature in combination with a known T/c characteristic line.

The control unit is identified above by reference numeral 27. For the location of the control unit 27 shown, the voltage of the transmitting signal generated in block 36 is controlled. On the other hand, if the control unit 27 were located between the transmitting amplifier 24 and the ultrasonic component 14, then the transmitting power would be controlled.

As already explained, the pressure p, which is present in the air spring 2, is determined with the aid of the control unit 27 to compensate the intensity I while considering the I/p characteristic line (FIG. 3c).

The determination of the running path of the sonic pulse from the ultrasonic transducer 14 to the reflector 16 and back is a relative method. The ratio of the running distance transducer 14/reflector 16 to the running distance transducer 14/reflector 20 or 22 is equal to the ratio of the running time of transducer 14/reflector 16 to the running time of transducer 14/reflector 20 or 22. If the running distance transducer 14/reflector 20 or 22 is known, then, in this way, the running distance transducer 14/reflector 16 and therefore the spring height can be determined.

As noted above, the adjustment of the intensity can take place either at the transmitter end after the signal generation 36 or after the power amplification 24 or, at the receiver end, in the controllable receiver amplifier 26. In the embodiment shown in FIG. 2, the control unit 27 is disposed between the signal generation 36 and the power amplification 24.

The block 40 identified as "Intensity Measurement I" is a first unit which measures the echo amplitude of the second reference reflector 22. A second unit comprising blocks 54 and 46 determines the pressure within the air spring.

The means for determining the temperature, which is present in the air spring 6, makes this determination from the running time of one of the two reference reflector echos. As shown in FIG. 3b, there is a functional relationship between the sonic velocity c and the temperature T. The spacing between the ultrasonic component 14 and the reference reflector 20 or 22 is known. Accordingly, there is a corresponding like functional relationship between the running time t of a pulse from the ultrasonic component 14 and the reference reflector 20 or 22 and back and the temperature present in the air spring. The running time is determined utilizing the component 48 "running time measurement (reference)". The computation of temperature then takes place in the downstream component 54 identified with the legend "temperature computation". This computation is made from the running time t, which is determined in component 48, and the T/c characteristic line or T/t characteristic line implemented in component 54.

It is understood that the foregoing description is that of the preferred embodiments of the invention and that various changes and modifications may be made thereto without departing from the spirit and scope of the invention as defined in the appended claims.

What is claimed is:

1. A pulse/echo method for making contactless measurements of the spacing between the axle and the chassis of an air spring suspended vehicle and to measure the pressure present in the air spring, the method comprising the steps of:

providing an ultrasonic arrangement including a transmitter/receiver component mounted on the chassis, a first reference reflector disposed at a first distance to said transmitter/receiver component and an end reflector fixedly mounted at the axle;

providing a second reference reflector disposed at a second distance to said transmitter/receiver component with said second distance being different from said first distance;

determining said spacing from a relative value of the running times of the ultrasonic pulses traversing said first and second distances;

converting sound reflected from said first and second reference reflectors into first and second sonic signals;

providing a control unit for controlling one of the transmitting signal power and the receiving amplification of said sonic signals to determine the pressure in said air spring;

adapting said control unit to control said one of said transmitting signal power and said amplification of said sonic signals so that the amplitude of the sound waves reflected from said first reference reflector remains at a constant value;

measuring the echo amplitude of said second reference reflector utilizing a first unit; and, determining the pressure in said air spring from the echo amplitude measured from said second reference reflector with the aid of an amplitude/pressure characteristic line and said instantaneous temperature.

2. The pulse/echo method of claim 1, wherein said amplitude of said sound waves is measured via said transmitter/receiver component.

3. The pulse/echo method of claim 1, wherein the temperature present in said air spring is determined from the echo running time of one of said first and second reference electrodes.

4. An arrangement for making contactless measurements of the spacing between the axle and the chassis in an air spring of an air-spring suspended vehicle and for measuring the pressure present in said air spring, the arrangement comprising:

a transmitter/receiver transducer component mounted on said chassis;

a first reference reflector mounted a first distance from said transmitter/receiver transducer component;

an end reflector mounted on said axle;

a second reference reflector mounted a second distance from said transducer component different from said first distance;

means for determining said spacing from a relative value of the running times of the ultrasonic pulses traversing said first and second distances;

means for converting sound reflected from said first and second reference reflectors into first and second sonic signals;

a control unit for controlling one of the transmitting signal power and the receiving amplification of said sonic signals;

means for measuring the amplitude of the sound waves reflected back from said first reference reflector via said transmitter/receiver transducer component;

said control unit being adapted to control said one of said transmitting power and said receiving Amplification of said sonic signals to maintain said amplitude at a constant value;

a first unit for measuring the echo amplitude of said second reference reflector; and, a second unit for determining the pressure in said air spring from the echo amplitude measured from said second reference reflector.

5. The arrangement of claim 4, further comprising means for determining the temperature in said air spring from the running time of one of the two reference reflector echos.

* * * * *